United States Patent [19]

Dewhirst

[11] Patent Number: 4,996,279
[45] Date of Patent: Feb. 26, 1991

[54] DISSYMMETRIC POLYMER MATERIALS

[75] Inventor: Kenneth C. Dewhirst, Houston, Tex.

[73] Assignee: Shell Oil Company, Houston, Tex.

[21] Appl. No.: 255,086

[22] Filed: Oct. 7, 1988

[51] Int. Cl.$^5$ .................... C08G 59/00; C08G 59/02
[52] U.S. Cl. ........................ 528/27; 528/96;
528/97; 528/98; 528/99; 528/104; 528/109;
528/117; 528/120; 528/122; 528/124; 528/407;
525/423; 523/445; 523/466; 523/468
[58] Field of Search ............... 528/96, 97, 98, 99,
528/104, 109, 124, 27

[56] References Cited

U.S. PATENT DOCUMENTS

| | | | |
|---|---|---|---|
| 3,364,178 | 1/1968 | Kreps et al. | 528/99 |
| 3,477,990 | 11/1969 | Dante et al. | 528/99 |
| 3,547,881 | 12/1970 | Mueller et al. | 528/99 |
| 3,733,305 | 5/1973 | Loewrigkeit | 528/99 |
| 3,794,619 | 2/1974 | Hasegawa et al. | 528/99 |
| 4,251,594 | 2/1981 | Davis et al. | 428/413 |
| 4,352,918 | 10/1982 | Whiteside, Jr. et al. | 528/89 |
| 4,657,954 | 4/1987 | Watanabe et al. | 528/104 |
| 4,684,678 | 8/1987 | Schultz et al. | 523/466 |
| 4,754,003 | 6/1988 | Monnier et al. | 525/490 |
| 4,795,791 | 1/1989 | Koenig et al. | 528/361 |
| 4,847,011 | 7/1989 | Dewhirst et al. | 260/351 |

FOREIGN PATENT DOCUMENTS

| | | |
|---|---|---|
| 249262 | 12/1987 | European Pat. Off. . |
| 249263 | 12/1987 | European Pat. Off. . |
| 0295126 | 12/1988 | European Pat. Off. . |
| 0149534 | 6/1981 | Fed. Rep. of Germany . |
| 0154985 | 5/1982 | Fed. Rep. of Germany . |
| 0211799 | 7/1984 | Fed. Rep. of Germany . |
| 0217810 | 6/1985 | Fed. Rep. of Germany . |
| 0238805 | 9/1986 | Fed. Rep. of Germany . |
| 61-167684 | 7/1986 | Japan . |
| 1063952 | 3/1989 | Japan . |

OTHER PUBLICATIONS

Bell, J. P., *J. Polymer Science*, A-2, 6, pp. 117–136 (1970).
Wrasidlo, W. et al., *J. Polymer Science*, A-1, 7, pp. 321–332 (1969).
Tess, R. W. et al., *Applied Polymer Science*, 2nd Ed., ACS Symposium Series 285, p. 934 (1985).

*Primary Examiner*—John Kight, III
*Assistant Examiner*—Frederick Krass

[57] ABSTRACT

Dissymmetric new epoxy polymer materials have improved processability because they can be cured at lower temperatures.

30 Claims, No Drawings

DISSYMMETRIC POLYMER MATERIALS

FIELD OF THE INVENTION

The present invention relates to new polymer materials which are epoxy polymers comprising linear molecules containing dissymmetric segments and having improved processability.

BACKGROUND OF THE INVENTION

Epoxy polymers have a variety of properties. Applicant has disclosed in his earlier co-pending applications new epoxy polymer materials with a good balance of modulus/glass transition temperature/toughness. However, some of these polymers can be difficult to process because of the high melting points of the reactants of polymers. Accordingly, Applicant realized that there was still a need for new epoxy polymers with better processability, which the present invention now provides.

SUMMARY OF THE INVENTION

The present invention is directed to a polymer composition comprising lightly crosslinked dissymmetric linear molecules having the repeating structures prior to crosslinking of the formula I

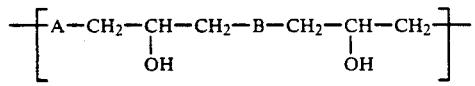

wherein (a) A is selected from the group consisting of

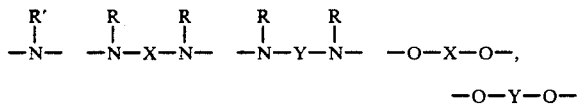

and mixtures thereof, and
B is selected from the group consisting of

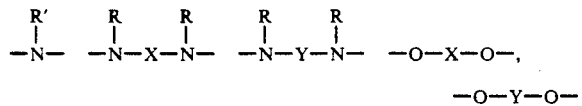

(b) each R is selected from the group consisting of unsubstituted or inertly substituted $C_1$-$C_{20}$ aliphatic, cycloaliphatic or aralkyl groups and each R' is selected from the group R plus any unsubstituted or inertly substituted aryl groups;

(c) said repeating structures are lightly crosslinked such that between 1 and 50 of said repeating structures per 100 total repeating structures are crosslinked to repeating structures of other molecules;

(d) X and Y each independently is a segment comprising stiff units (SU and SU', respectively) and flexible units (FU and FU', respectively), which stiff units and flexible units are interconnected, with the proviso that in about 50% or more of the total segments X plus Y the stiff and flexible units are interconnected to form a segment which is dissymmetric along its linear chain axis;

(e) said stiff units, SU and SU', are independently selected from the groups consisting of unsubstituted and substituted aryl, and non-interfering heterocyclic rings;

(f) said flexible units, FU and FU', are independently selected from the group of

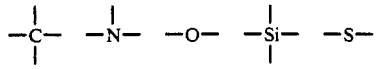

and (g) the ratio of the number of stiff units to flexible units in said X segment (SU/FU) is equal to or greater than the ratio of the number of stiff units to flexible units in said Y segment (SU'/FU').

PREPARATION

The polymers of the invention are prepared by the reaction between a diepoxide and diphenol which requires the presence of a condensation catalyst, as is well known in the art of epoxy polymers or an amine component or mixtures of a diphenol and an amine component. When required, typically, the catalyst is a basic catalyst. The process and the conditions of the preparation process are, thus, conventional in the art and include those disclosed in the aforementioned allowed co-pending applications Ser. Nos. 871,951 and 871,952, filed June 6, 1986, which disclosures are incorporated herein by reference.

The polymers of the invention are prepared from a diepoxide component and a diphenol or an amine component or mixture of a diphenol and an amine compound contains at least one dissymmetric segment in the polymer. A prepolymer can be prepared which can be stored for later reaction or which can be reacted in the presence of the condensation catalyst to form said linear polymers.

An important part of the present invention is the stiff units (SU and SU') and the flexible units (FU and FU') which are interconnected to form the segments X and Y and which are selected in appropriate types and ratios so that about 50% or more of the total segments X plus Y are dissymmetric along the linear chain axis. Preferably, about 55% or more of the total segments X plus Y are dissymmetric. More preferably, about 75% or more of the total segments are dissymmetric. In some instances, the best processability is obtained when about 100% of the total segments are dissymmetric.

The term "dissymmetric" or "longitudinal dissymmetric segment" as used herein means a segment in which the stiff and/or flexible units are assembled in such a way that the two linear halves of the segment are not mirror images of each other.

STIFF UNITS

The stiff units are unsubstituted or inertly substituted aryl, and non-interfering heterocyclic rings. Suitable substituent groups include Cl, Br, or $C_1$ to $C_5$ alkyl groups and the like.

The term "aryl ring" refers to unsubstituted and substituted benzene rings and includes the benzene ring and annulation of benzene to give naphthalene, anthracene, phenanthrene and the like.

The term "heterocyclic ring" refers to unsubstituted and substituted heterocyclic rings and includes 5-6 membered heterocyclic rings including pyrrole, pyridine, furan, thiophene, imidazole, oxazole, thiazole, dibenzothiophene, carbazole and the like. In the selection of heterocyclic rings, O and S heterocyclics are generally suitable. However, in the case of N heterocyclics, care should be taken so that the N is not strongly basic so that homopolymerization of the epoxide occurs.

FLEXIBLE UNITS

By use of the term "flexible unit" is meant those units that permit rotation at an angle to the linear axis of the polymer. Examples of flexible units include Broad group     Examples within the broad group $$-\underset{|}{\overset{|}{C}}- \quad -\underset{\underset{H}{|}}{\overset{\overset{H}{|}}{C}}-, -\underset{\underset{|}{|}}{\overset{\overset{H}{|}}{C}}-, -\underset{\underset{CH_3}{|}}{\overset{\overset{CH_3}{|}}{C}}-, -\overset{\overset{O}{\|}}{C}-, -\underset{\underset{F}{|}}{\overset{\overset{F}{|}}{C}}-,$$

$$-\underset{|}{N}- \quad -\underset{|}{N}-\overset{\overset{O}{\|}}{C}-$$

$$-O- \quad -O-\overset{\overset{O}{\|}}{C}-$$

$$-\underset{|}{\overset{|}{Si}}- \quad -O-\underset{|}{\overset{|}{Si}}-O-$$

$$-S- \quad , \quad -\overset{\overset{O}{\|}}{\underset{\underset{O}{\|}}{S}}-$$

SELECTION OF STIFF AND FLEXIBLE UNITS FOR STIFF AND FLEXIBLE SEGMENTS

One aspect of the invention is the selection and location of the stiff units and flexible units for the stiff segments and flexible segments. The stiff units and optional flexible units are attached in such a manner that the end units of segments X and Y are always stiff units. The stiff segment can be located in either the diphenol or amine component or in the diepoxide component or in each of the components. While the invention is generally described in terms of one X and one Y segment, it should be understood that polymers of the invention can be prepared having more than two different components, and, thus, more than one kind of X and/or Y segments.

In one preferred embodiment of the invention, the ratio of stiff units to flexible units in the stiff segment is greater than the ratio of the stiff units to flexible units in the flexible segment $+0.5$.

In one embodiment of the invention, the average number of total stiff units divided by the average number of total flexible units is between about 2 and about 20, and, preferably, between about 2.5 to about 10.

In another embodiment of the invention, the ratio of the amount of stiff segments a in the molecule and flexible segments b in the molecule is such that the ratio.

$$\frac{a}{a+b}$$

is less than or equal to one, preferably, more than zero and less than or equal to one, and more preferably, between about 0.4 to about 0.6.

DIPHENOL COMPONENT

The diphenol components employed herein have the structure HO—X—OH and HO—Y—OH wherein X represents the stiff segment specified above and Y represents the flexible segment specified above.

Dissymmetric diphenols are known in the art and are prepared by conventional procedures used to prepare stiff units containing hydroxy sustituents which are used alone or combined with flexible units in known manner to form dissymmetric diphenols. For example, although 4-hydroxyphenyl 4-hydroxynaphthyl sulfone (mixed isomers) is a novel compound, it is prepared in a conventional manner by the reaction of 4-chlorobenzenesulfonyl chloride with 1-chloronaphthylene in the presence of anhydrous aluminum chloride followed by treatment of the resulting product with potassium hydroxide. In a similar manner, known in the crude form from Japanese patent application 61/167,684, published July 29, 1986, N,N'-(3-hydroxyphenyl)phthalimide-4-carboxamide was prepared in a conventional manner by reacting trimellitic acid chloride with the corresponding m-aminophenol in acetic acid. Other dissymmetric diphenols can be prepared following procedures similar to the above.

Diglycidyl ethers of dissymmetric diphenols have lower melting points than diglycidyl ethers of the corresponding symmetrical diphenols. This feature allows the polymers of the invention prepared from such dissymmetric diphenols or their corresponding glycidyl ethers or amines to be cured more readily. Mixtures of position isomers of a dissymmetric diphenol or corresponding glycidyl ether or amines have even lower melting points than a single position isomer of the same compound and can be preferred in some cases.

Other diphenol components useful herein are the imide-derived diphenols, such as those compounds disclosed in U.S. pat. No. 3,821,162 and reported by J. E. McGrath, 29th National SAMPE Symposium Apr. 3–5, 1984, page 447, the disclosures of which are incorporated herein by reference.

One group of symmetric diphenol components particularly useful herein in combination with dissymmetric diphenols or glycidyl ethers thereof or amines are represented by the formula

in which R and $R_1$ when taken collectively with the connector carbon C are selected from the group consisting of cyclohexyl and alkyl-substituted cyclohexyl, and when taken separately are from the group consisting of hydrogen, alkyl, cyclohexyl, phenyl, alkyl-substituted cyclohexyl, alkyl-substituted phenyl, halogen- substituted cyclohexyl and halogen-substituted phenyl groups with the total number of carbon atoms in the group or groups attached to said connector carbon atom not exceeding about eighteen and the number of carbon atoms, in any alkyl-substituent not exceeding about six. The preferred diphenols have the hydroxyl groups in the 4,4' positions, but compounds with hydroxyls in the 2,2', 3,3' and 2.4' and other arrangements can also be used. R and $R_1$ suitably are methyl, ethyl, isobutyl, n-nonyl, n-heptadeycl and the like. Other dihydric phenols can also be employed, excepting those which have two hydroxyl groups in the ortho positions on a single benzene ring which do not form substantially linear molecules.

Preferably, it is desired that the diphenol compound be meta or para derivatives as opposed to ortho structures.

Still another group of diphenol compounds are those distinguished from BPA by the presence of 2 or more flexible groups which are used to connect additional stiff units in the linear chain of a segment. Still another group of diphenol compounds are those based on phthalocyanine. The two groups of compounds in the symmetrical form are disclosed in the earlier referenced allowed U.S. patent application of this same Applicant.

The dihydric phenols employed in the process of the invention can be substantially 100 percent pure, or can be a technical grade of somewhat lower purity. Concentrates of diphenol containing, for example, 90 to 100 percent of the pure compound can be used.

Examples of dissymmetric and symmetric diphenols include:

polymer properties that the crude reactant be free of monoepoxide and of monohydric phenol or alcohol. Suitable diepoxide can be prepared from a diphenol of the type previously described herein above. Concentrates of diepoxide containing between 90 to 100 percent of pure compound are preferred for better polymer properties.

Dissymmetric diepoxides are known in the art as are the diphenols from which they are prepared by conventional procedures used to prepare epoxides of diphenols containing stiff units bearing hydroxy sustituents which are used alone or combined with flexible units in known manner to form dissymmetric diphenols.

Examples of suitable dissymmetric and symmetric diepoxides include:
N,N'-bis(3-glycidyloxyphenyl)pyromellitimide,
N,N'-bis(3-glycidyloxyphenyl)phthalimide-4-carboxamide,
4-glycidyloxyphenyl-4-glycidyloxynaphthyl sulfone and the like.

The diepoxide used in the invention can also have the structure

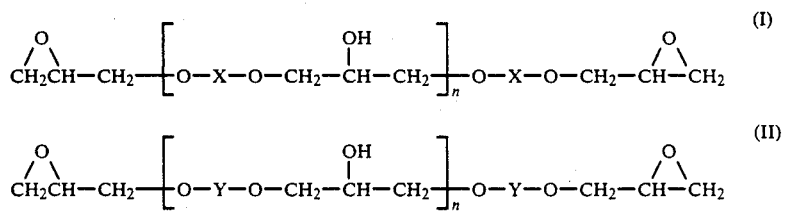

N,N'-bis(3-hydroxyphenyl)phthalimide-4-carboxamide,
4-hydroxyphenyl 4-hydroxynaphthyl sulfone,
9,9-bis(4-hydroxyphenyl)fluorene,
10,10-bis(4-hydroxyphenyl)anthrone,
9,9-bis(4-hydroxyphenyl)phenanthrone,
9,9-bis(4-hydroxyphenyl)-9,10-dihydroanthracene,
3,3-bis(4-hydroxphenyl)-4,5-benzodihydrofuran, and the like.

DIEPOXIDE COMPONENT

One component of the polymer compositions of the invention is a diepoxide having two epoxide groups in the terminal or non-terminal positions in the molecule, usually in the form of an oxygen atom bound to two terminal carbon atoms of an alkyl group although the epoxide can be on a ring, such as a cyclohexyl ring and the like. Suitable diepoxides include terminal diepoxyalkanes, such as 1,2-epoxy-3,4-epoxybutane, 1,2-epoxyhexane, 1,2-epoxy-7,8-epoxyoctane and the like. Others include terminal diepoxies containing ether linkages, such as bis(2,3-epoxypropyl)ether, bis(2,3-epoxy-2-methlpropyl)ether and the like; diglycidyl ether of alpha, omega glycols, such as the diglycidyl ethers of ethylene glycol, triethylene glycol tetraethylene glycol and the like and diglycidyl ethers of dihydric phenols.

The diglycidyl ethers of dihydric phenols which are generally suitable for use in the present invention include the diglycidyl ethers of the same phenol or of different phenols and the phenols in the diglycidyl ether reactant can be the same as the phenols used as the phenol component in the reaction or they can be different.

In preparing the polymers of the invention, the diepoxide reactant can be a pure diepoxide or a crude mixture containing a substantial proportion of diepoxide, e.g., 70% or more. It is, however, important for good wherein X and Y are dissymmetric or symmetric stiff and flexible segments as previously defined and the number "n" has a value of from about 0 to about 6, preferably from about 0 to about 2, most preferably 0.

AMINE COMPONENT

The amine component employed in making the polymers of the present invention is selected from the group consisting of primary amines, bis-secondary amines or mixtures thereof.

The primary amines have the formulas

and the bis-secondary amines have the formulas

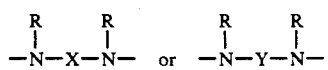

wherein R is selected from unsubstituted or inertly substituted $C_1$ to $C_{20}$ aliphatic, cycloaliphatic or aralkyl groups and X and Y are the previously defined dissymmetrical or symmetrical segments. Examples of R include methyl, ethyl, isopropyl, cyclohexyl, benzyl, and the like. R' includes the above plus unsubstituted and substituted aryl groups, such as phenyl and tolyl. Preferably, each R is selected from $C_1$ to $C_{10}$ alkyl groups and R' is phenyl.

Examples of primary amines include aniline, 2,6-dimethylaniline, 2,4-dimethylaniline, 2,6-diethylaniline, N-aminophthalimide, 2,6-diisopropylaniline, tolylamine, alpha-naphthylamine, 3-aminobenzothiophene, 1-aminoadamantane, norbornylamine, and the like. Examples of symmetric bis-secondary amines include N,N'dimethyl-p-phenylenediamine, bis(N-sec-butyl-4-aminophenyl)methane, alpha,alpha'-bis(N-methyl-4-aminophenyl)-p-diisopropylbenzene, N,N'-dimethyl-4,4'-diaminodiphenyl sulfone and the like.

Dissymmetric bis-secondary amines are also known in the art and are prepared by conventional procedures similar to these used to prepare symmetrical bis-secondary amines. The dissymmetrical amines containing stiff units bearing amino groups, which are used alone or combined with flexible units in known manner to form dissymemtric bis-secondary amines. For example, (4-methylaminophenyl) (1-methylaminonaphthyl) methane or sulfone or the like.

Diglycidyl ethers of dissymmetric bis-secondary amines have lower melting points than corresponding symmetrical bis-secondary amines. This feature allows the polymers of the invention prepared from such dissymmetric di-secondary amines or digycidyl ethers thereof to be cured more readily. Mixtures of position isomers of an dissymmetric diphenol or corresponding glycidyl ether have even lower melting points than a single position isomer of the some compound and can be preferred in some cases.

LIGHT CROSSLINKING

An important aspect of the present invention relates to the light crosslinking of the resulting thermoplastic polymers molecules to from the resulting polymer matrix. The term "light crosslinking" refers to the crosslinking of between 1 to about 50 out of each 100 repeat units to other repeat units of other molecules, e.g., formula 1, of the thermoplastic polymer. Preferably, the light crosslinking density is between about 2 and about 25 repeat units per 100 repeat units.

There are several known techniques that can be used to obtain lightly crosslinked matrices. One technique involves the use of a slightly greater number of epoxide groups than phenol groups. Another technique is to incorporate an appropriate amount of tri- or higher functional epoxide or tri- of higher functional phenolic or amine component in the preparation of the polymer.

A third technique involves the addition of crosslinking agents, such as triepoxides and the like, to the resulting thermoplastic polymer. These kinds of techniques are generally known in the art and are also described in Applicant's above referred to allowed U.S. patent applications, the disclosures of which are incorporated herein by reference. The crosslinking agents can be symmetrical or dissymmetrical molecules. The same principals of synthesis and advantages of lower melting point properties in melt polymerization are true for dissymmetric crosslinking agents as for the dissymmetrical diglycidyl ethers, diphenols or diamines discussed above.

POLAR UNITS

In one preferred embodiment of the compositions of the invention, the incorporation of polar units into the linear chain in combination with stiff units comprising benzene or fused two to four polycyclic aromatic or five to six membered heterocyclic rings gives rise to improved solvent resistance, particularly with regard to strong solvents, such as methyl ethyl ketone, methylene chloride and the like which are often used as paint stripping solvents. Accordingly, when such properties are desired, the lightly crosslinked polymers of the invention can be made so that the about 50% or more of the total segments X plus Y contain at least one polar unit by the selection and incorporation into the segments forming the linear chain of the polymer polar units having note more than two atoms in any side chains of the unit which are other than hydrogen atoms. The polar units useful in the polymers of the present invention include

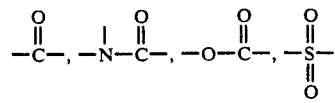

and the like.

The incorporation of the polar groups can be in the flexible unit or the ring portion of the stiff unit of the segment as long as about 50% or more of the total segments of the polymer contain at least one polar unit.

Preferably, there are at least two polar units in the molecule and while they can be in either segment or in the same segment, it is preferred that the polar units be in different segments. For example, at least one polar unit be in the diepoxide component and at least one other polar unit can be in the diphenol or amine component.

Preferably, about 55% or more of the total segments X plus Y contains at least one polar unit as a part of the linear chain, said polar unit having not more than two side chain atoms other than hydrogen attached to a central C, N, or S atom. More preferably, about 75% or more of the total segments X plus Y contain at least one polar unit. The best solvent resistant properties are usually obtained when there is at least one polar unit in all (about 100%) of the total X plus Y segments.

In this embodiment the ratio of stiff units to flexible units in the stiff segment is equal to the ratio of the stiff units to flexible units in the flexible segment. The average total stiff units divided by the average total flexible units is about 2 to about 20, preferably about 2.5 to about 10, and the ratio.

$$\frac{a}{a+b}$$

is about one, preferably between about 0.4 to about 0.6.

USES

The polymer compositions of the invention have application where toughness, modulus and other properties are useful and particularly in the automotive and aerospace industry where high performance obtainable with the present compositions of the invention is required coupled with resistance to solvents, such as methyl ethyl ketone, methylene chloride and the like. The dissymmetric polymers of the invention have the added advantage of improved processability because the lower melting points of the dissymmetric monomers allow the polymers to be cured more readily.

The polymers of the invention are preferably used with a reinforcing material. Suitable reinforcing materials include, glass fibers, carbon fibers, Kevlar, boron calcium carbonate, talc, alumina, asbestos, and the like. The fibrous reinforcing material can be present in the composition in an amount effective to impart increased strength and stiffness to the cured composition, generally between about 40 to about 95 weight percent, usually about 60 to about 80 weight percent, based on the weight of the total composition.

The compositions of the invention preferably have a glass transition temperature of at least about 150° C., a flex modulus of at least about 350 KSI and a fracture toughness of at least about 1000 psi √in.

ILLUSTRATIVE EMBODIMENTS

The invention is illustrated by the following embodiments which should not be regarded as limiting the invention in any way. The products were confirmed by elemental, nuclear magnetic resonance spectral analysis and the like as necessary.

EMBODIMENT 1

4-Chlorophenyl 4-chloronaphthyl sulfone (CPNS) Mixed Isomers p-Chlorobenzenesulfonyl chloride, 0.1 mol, anhydrous aluminum chloride, 0.1 mol, 1-chloronaphthylene, 0.11 mol, and 100 ml of nitromethane were mixed at room temperature under nitrogen. The mixture was stirred at 80° C. for 3 hours, cooled to room temperature and decomposed with 3N hydrochloric acid. The organic layer was diluted with 50 ml of methylene chloride and washed with 2 portions of 1N hydrochloric acid followed by pure water. HPLC analysis of the organic layer indicated a yield of 85% CPNS. The organic layer was treated with decolorizing carbon, filtered, and evaporated to give 25 g of dark liquid.

A small sample of the product was adsorbed on a silica column and eluted with 10% methyl isobutyl ketone-hexane to give a cluster of peaks, mol wt 336 by mass spectroscopy.

EMBODIMENT 2

4-hydroxyphenyl 4-hydroxynaphthyl sulfone (PNS) Mixed Isomers

Crude CPNS, 12 g, 15 g of 85% potassium hydroxide, and 50 ml of methanol were sealed in an autoclave under nitrogen and stirred at 200° C. for 3 hours. The reaction mixture was cooled, evaporated to dryness, and extracted 3 times with chlorobenzene. The residue was dissolved in water, acidified with hydrochloric acid, and taken up in a 40% methyl ethyl ketone-methylene chloride mixture. The organic layer was evaporated, and the residue was adsorbed on a silica column and eluted with 35% methyl ethyl ketone-hexane to give a viscous, amber liquid.

NMR analysis suggested that the main isomer was 4-hydroxynaphthyl 4-hydroxy-1-phenyl sulfone.

The material was dried at 170° C. and 1 mm for 2 hours to give the desired product as a solid, m.p. 152°–163° C.

EMBODIMENT 3

4-Glycidyloxyphenyl 1-glycidyloxynaphthyl sulfone (DGPNS) Mixed Isomers

PNS, 18 g, was dissolved in isopropyl alcohol and treated with 10 equivalents of epichlorohydrin. Sodium hydroxide, 2.4 equivalents, was then added portionwise at 80° C., and the brine layer was removed after each addition. The organic layer was stripped in vacuo at 130° C., and the residue was dissolved in methyl isobutyl ketone. The resulting solution was treated with 5% caustic solution at 88° C. for 2 hours cooled, and washed with water to neutrality. The organic layer was stripped to give 21.5g of the desired product as a dark, viscous liquid, WPE 236, Saponifiable chlorine 0 0.91% w.

EMBODIMENT 4

4-Methoxyphenyl 4-methoxy-1-naphthyl sulfone (EPNS)

p-Methoxybenzenesulfonyl chloride, 2.0 mol, anhydrous stannic chloride, 2.25 mol, 1-methoxynaphthalene, 2.25 mol, and 3 l of o-dichlorobenzene were mixed at room temperature under nitrogen. The mixture was stirred at room temperature overnight (ca 7 hours needed) and decomposed with 3N hydrochloric acid. The organic layer was diluted with 1250 ml of nitromethane and washed with 2 portions of 1N hydrochloric acid followed by pure water. The organic layer was treated with magnesium sulfate, filtered, evaporated, extracted with hot toluene and dried at 120° C. for two hours to give 577 g, 88% yield, m.p. 160°–162° C.

The structure was confirmed by Mass Spec (M/Z=328) and NMR. HPLC indicated the purity was 99.7%.

EMBODIMENT 5

4-Hydroxyphenyl 4-Hydroxy-1-naphthyl sulfone (PNS)

EPNS, 505 g (1.54 mol), 500 g (9.25 mol) of sodium methoxide, and 3 l of ethylene glycol were heated under nitrogen with a short Vigreux column and distilled until the pot temperature reached 205° C. and the vapor temperature 180° C., at which time ca 490 ml of distillate had been collected. The reaction mixture was cooled, poured into 4 l of chilled water and acidified with concentrated HCl. The precipitate was filtered, washed twice with water, dried, and extracted with hot o-dichlorobenzene (140° C.) to give after drying 441 g (96% yield) of product, m.p. 198°–199° C. purity 98.4% by HPLC. The material eluted identically with the major isomer of PNS previously prepared.

EMBODIMENT 6

4-Glycidyloxyphenyl 4-Glycidyloxy-1-naphthyl sulfone (DGPNS)

PNS, 168 g, was dissolved in isopropyl alcohol and treated with 10 equivalents of epichlorhydrin. Sodium hydroxide, 2.4 equivalents, was then added portionwise at 80° C., and the brine layer was removed after each addition. The organic layer was stripped in vacuo at 130° C., and the residue was dissolved in methyl isobutyl ketone. The resulting solution was treated with 5% caustic solution at 88° C. for 2 hours, washed with water to neutrality, filtered, and cooled to give 158 g (68% yield) of product, m.p. 134°–136° C. The filtrate was evaporated to 54 g (23% yield) of product with ca 15% of oligomers. The crystallized material was degassed in vacuo at 160° C. to give product, WPE 217, Saponifiable Cl 0.005% w, oligomer 5% m.

The structure of the product was supported by NMR, but showed the presence of 2% m methyl isobutyl ketone.

EMBODIMENT 7

4-Methylaminophenyl sulfone (NMDDS)

4-Chlorophenyl sulfone, 4 g was heated with 50 ml of 40% aqueous methyl amine in an autoclave overnight at 200° C. The mixture was cooled, filtered, washed with water, and dried to give 4g of product, m.p. 176°–178° C. This material was recrystallized from 10% N- methylpyrrolidone-hexane to give a product m.p. 178°-180° C. and contained about 4% methylaminophenyl dimethylaminophenyl sulfone impurity. In order to prepare material free of impurity th method of L. F. Fieser et al., *J.A.C.S.*, 67, 1984 (1945) was used and the resulting product had a m.p. of 179°-180° C. and was essentially 100% pure.

EMBODIMENT 8

4-Aminophenyl 4-methylaminophenyl sulfone (MMDDS)

This material was prepared for use as a dissymmetric crosslinking agent by extraction of the crude product, N,N'-dibenzenesulfonyl-4,4'-bis(methylamino)phenyl sulfone obtained from the above Fieser procedure above, with 1N sodium hydroxide. The precipitated sodium salt was filtered off and hydrolyzed with sulfuric acid as in the reference to give the desired product, m.p. 163° C.

EMBODIMENT 9

N,N'-bis(3-hydroxyphenyl)phthalimide-4-carboxamide (BPAITm)

m-Aminophenol, 2 mol, was added slowly to 1 mol of trimellitic acid chloride in acetic acid and stirred under nitrogen for 1 hour Pyridine, 1 mol, was then added and the mixture was stirred 1 hour at room temperature and overnight at reflux. The mixture was cooled and filtered to give crude product, m.p. 276°-279° C. HPLC showed the material to contain about 5% imide-acid as impurity. Pure product was obtained by washing the crude product with aqueous sodium bicarbonate.

EMBODIMENT 10

N,N'-bis(3-glycidyloxyphenyl)phthalimide-4-carboxamide (DGBPAITm)

BPAITm was refluxed under nitrogen with a 69 molar excess of epichlorohydrin and 0.1%w tetrabutyl ammonium bromide for 4 hours. The mixture was cooled, washed with aqueous sodium dihydrogen phosphate, concentrated to 1/3 the original volume and precipitated with diethyl ether to give a low-melting solid similar to that reported by Y. Saito et al., Japanese patent application 61/167,684 (1986) and was about 80% pure by HPLC. The crude product was dissolved in methyl ethyl ketone, adsorbed on a silica column, and eluted with 45% methyl ethyl ketone-hexane to give white crystals, m.p. 162°-166°C. WPE 248, Saponifiable Cl 0.17% w, and monomer concentration of 95%.

EMBODIMENT 11

Dissymmetric Lightly Crosslinked Polymers

The polymer was made by melting polymer, curing agent, and crosslinker (diaminodiphenyl sulfone) in a mole ratio of 1.0/0.8/0.2 at 170° C. in a vacuum Erlenmeyer flask, degassing at 1 mm Hg until bubbling ceased, pouring the molten pre-polymer into a mold (two glass plates treated with release agent, preheated in a forced draft oven at 170° C.) and curing the polymer at the prescribed cure cycle. At the end of the cycle, the casting was removed from the oven and allowed to cool below its Tg and the plates popped loose. The resulting polymers and their properties are shown in Table 1 below:

TABLE 1

| | Dissymmetric Solvent Resistant Lightly Crosslinked New Polymer Materials | | | | | | | | |
|---|---|---|---|---|---|---|---|---|---|
| Diepoxide[1] | Diepoxide Tm °C. | Polymer Tg °C. | Gel Time Min. | E rt KSI | E h/w KSI | Kq PSI in | MEK[2] 14 Day % | MC[3] 14 Day % | $H_2O$ Equil % |
| DGPNS[4] | liquid | 195 | 29 | 520 | 390~1000 | | 0.1 | 1.8 | 3.2 |
| DGBPAITm[5] | 163 | 201 | 12 | 550 | 430~1000 | | 0.1 | 0.8 | 5.0 |

[1]Cured with NMDDS at 170° C./16 hours + 220° C./4 hours.
[2]Methyl ethyl ketone.
[3]Methylene chloride.
[4]4-glycidyloxphenyl 4-glycidyloxynaphthyl sulfone (mixed isomers)
[5]N,N'-bis(3-glycidyloxyphenyl)phthalimide-4-carboxamide.

These dissymmetric lightly crosslinked polymers had improved processability was well as unexpected resistance to very strong solvents, such as methyl ethyl ketone and methylene chloride, which are used as paint stripping solvents.

The flexural properties of the neat polymers were evaluated according to ASTM D790 method using ⅛" thick specimens. Specimens were tested both in Dry (at room temperature and at 75% R.H.) and Hot Wet (after immersion in boiling water for 48 hours, test at 95° C., 5 minutes equilibration time) conditions.

Fracture toughness, Kq, was measured using mini-compact tension specimens (see W. B. Jones et al., *Am. Chem. Soc. Div. Polym. Chem. Prepr.*, 22, 1981). All specimens were slotted to a Chevron shape and then precracked with a razor blade.

Selling in solvents was evaluated by measuring weight gain per unit of initial weight after immersion in solvent for a specified time at room temperature.

Again, these dissymmetric lightly crosslinked polymers had improved processability in melt polymerization because of their lower melting points, as compared to the polymers made from the corresponding symmetrical epoxides, diphenols or amines as well as unexpected resistance to very strong solvents, such as methyl ethyl ketone and methylene chloride, which are used as paint stripping solvents.

Following procedures similar to those described in Embodiment 8 above, a lightly crosslinked polymer can be prepared using 4-aminophenyl 4-methylaminophenyl sulfone (MMDDS) as a dissymmetric crosslinking agent.

What is claimed is:

1. A polymer composition consisting essentially of lightly crosslinked dissymmetric linear thermoplastic polymer molecules prepared from a diepoxide and at least one diphenol, primary amine or bis-seeondary amine and having the repeating structures prior to crosslinking of the formula

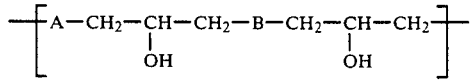

wherein said thermoplastic polymer molecules have substantially no epoxy functionality prior to crosslinking, and wherein (a) A is selected from the group consisting of

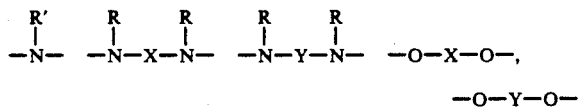

and mixtures thereof, and
B is selected form the group consisting of

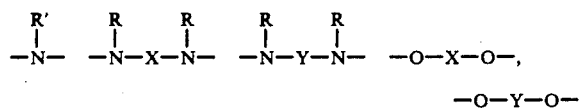

(b) R and R' are independently selected from the group consisting of unsubstituted or inertly substituted $C_1$-$C_{20}$ aliphatic, cycloaliphatic or aralkyl groups, and each R' also is independently selected from the group of R plus any unsubstituted or inertly substituted aryl groups;
(c) said repeating structures are lightly crosslinked such that between 1 and 50 of said repeating structures per 100 total repeating structures are crosslinked to repeating structures of other molecules;
(d) X and Y each independently is a segment comprising stiff units (SU and SU', respectively) and flexible units (FU and FU', respectively), which stiff units and flexible units are interconnected, with the proviso that in about 50% or more of the segments X plus Y the stiff and flexible units are interconnected to form a segment which is dissymmetric along its linear chain axis;
(e) said stiff units, SU and SU', are independently selected from the groups consisting of unsubstituted and substituted aryl, and non-interfering heterocyclic rings;
(f) said flexible units, FU and FU', are independently selected form the group of

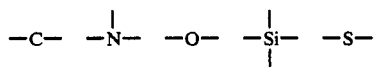

and
(g) the ratio of the number of stiff units to flexible units in said X segment (SU/FU) is equal to or greater than the ratio of the number of stiff units to flexible units in said Y segment (SU'/FU').

2. The composition according to claim 1 wherein the dissymmetric segment is in the group —O—X—O— or —O—Y—O—.

3. The composition according to claim 2 wherein the dissymmetric segment is derived from the 4-hydroxyphenyl 4-hydroxynaphthyl sulfone, the diglycidyl ether thereof or a mixture of the two.

4. The composition according to claim 2 wherein the dissymmetric segment is derived from N,N'bis(3-hydroxyphenyl)phthalimide-4-carboxamide, the diglycidyl ether thereof or a mixture of the two.

5. The composition according to claim 1 wherein about 75% or more of the total segments X plus Y are dissymmetric.

6. The composition according to claim 1 wherein the dissymmetric segment is derived from 4-aminophenyl 4-methylaminophenyl sulfone.

7. The composition according to any one of claims 1, 2, 5 or 6 wherein the average number of total stiff units divided by the average number of total flexible units is greater than 4 and less than about 20.

8. The composition according to any one of claims 1, 2, 5 or 6 wherein the average number of total stiff units divided by the average number of total flexible units is between 5 and about 10.

9. The composition according to any one of claim 1, 2, 5 or 6 wherein the ratio of $$\frac{a}{a+b}$$

is more than zero and less then 1 wherein a equals the amount of stiff segments in the molecule and b equals the amount of flexible units.

10. The composition according to any one of claims 1, 2, 5 or 6 wherein the ratio of $$\frac{a}{a+b}$$

is between about 0.4 and 0.6 wherein a and b are previously of defined.

11. The composition according to any one of claims 1, 2, 5 or 6 wherein the ratio of $$\frac{SU}{FU} > \frac{SU'}{FU'} + 0.5.$$

12. The composition wherein the composition of claim 1 is lightly crosslinked such that between 1 and about 20 repeating structures from different molecules per 100 of said repeating structures are crosslinked together.

13. The composition of claim 12 wherein between 3 and 10 per 100 repeating structures are crosslinked together.

14. The composition of claim 1 which further comprises a crosslinking agent.

15. The composition of claim 14 wherein an effective amount of crosslinking agent is employed such that between about 1 and about 50 repeating structures from different molecules per 100 of said repeating structures are crosslinked together during cure.

16. The composition of claim 14 wherein further comprises a fibrous reinforcing material.

17. The composition of claim 16 wherein the fibrous reinforcing material is selected from the group consisting of glass fibers, carbon fibers, boron fibers and Kevlar fibers.

18. The cured composition according to any one of claims 1, 2, 5 or 6 having a glass transition temperature of at least about 150° C.

19. A prepreg comprising the composition of claim 12 and a fibrous reinforcing material.

20. An article of manufacture prepared from the prepreg of claim 19.

21. The composition of claim 1 having a glass transition temperature of at least about 150° C., a flex modulus of at least 350 KSI and a fracture toughness of at least 1,000 psi $\sqrt{\text{in}}$.

22. The composition of claim 14 wherein the crosslinking agent is an amine.

23. The composition according to claim 1 wherein 50% or more of the segments X plus Y contain at least one polar unit having not more than two atoms in any side chains of the unit which are other than hydrogen atoms.

24. The composition according to claim 23 wherein the polar unit is selected from

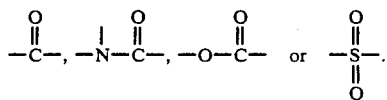

25. The composition according to claim 24 wherein about 55% or more of the total segments X plus Y contain at least one polar unit.

26. The composition according to claim 24 wherein about 75% or more of the total segments X plus X contain at least one polar unit.

27. The composition according to claim 26 wherein about 100% of the X plus Y total segments contain at least one polar unit.

28. The composition according to any one of claims 1, 2, or 3 wherein the dissymmetric segment is derived from the diglycidyl ether of 4-hydroxyphenyl 4-hydroxynaphthyl sulfone.

29. The composition according to claim 28 wherein A is derived from 4-hydroxyphenyl 4-hydroxynaphthyl sulfone.

30. The composition according to claim 28 wherein A is derived from N,N'-dimethyl-4,4'-diaminodiphenyl sulfone.

* * * * *